US008354099B2

(12) United States Patent
Maor et al.

(10) Patent No.: US 8,354,099 B2
(45) Date of Patent: Jan. 15, 2013

(54) SKIN-CARE COMPOSITIONS AND USES THEREOF

(75) Inventors: Zeev Maor, Dead Sea (IL); Tamar Zioni, Motza Ilit (IL)

(73) Assignee: Ahava-Dead Sea Laboratories Ltd., Mobile Post Dead Sea (IL)

( * ) Notice: Subject to any disclaimer, the term of this patent is extended or adjusted under 35 U.S.C. 154(b) by 391 days.

(21) Appl. No.: 12/574,159

(22) Filed: Oct. 6, 2009

(65) Prior Publication Data

US 2010/0111878 A1  May 6, 2010

Related U.S. Application Data

(60) Provisional application No. 61/136,834, filed on Oct. 7, 2008.

(51) Int. Cl.
*A61K 8/97* (2006.01)
*A61Q 5/00* (2006.01)
*A61Q 9/00* (2006.01)

(52) U.S. Cl. .............. 424/74; 424/762; 424/59; 424/45; 424/63; 510/119; 510/130

(58) Field of Classification Search ........................ None
See application file for complete search history.

(56) References Cited

U.S. PATENT DOCUMENTS

| 5,843,911 A * | 12/1998 | Nakahara et al. ............... 514/38 |
| 2006/0083708 A1 | 4/2006 | Schwartz |
| 2006/0198810 A1 | 9/2006 | Murray et al. |
| 2007/0166267 A1 | 7/2007 | Majewski et al. |
| 2007/0212433 A1 | 9/2007 | Smidt et al. |
| 2007/0224154 A1 | 9/2007 | Brumbaugh et al. |

FOREIGN PATENT DOCUMENTS

| DE | 100 20 874 A1 | 5/2001 |
| EP | 1 344 515 A1 | 9/2003 |
| JP | 2006-117592 A | 5/2006 |
| WO | 95/02128 A1 | 1/1995 |
| WO | 99/02128 A1 | 1/1999 |
| WO | 00/40255 A1 | 7/2000 |

OTHER PUBLICATIONS

Ingolfsdottir, K., "Bioactive compounds from Iceland moss" Proceedings of the Phytochemical Society of Europe, 200, vol. 44, pp. 25-36.*
Dohi, K., et al. "Fibroblast growth-promoting agent containing kajiichigoside F1 for skin and food compositions". 2004. Maruzen Pharmaceuticals Co., Ltd., Japan. XP002569024.
Gülçin, I., et al. "Determination of antioxidant activity of lichen cetraria islandica". Journal of Ethnopharmacology. 2002, vol. 79, pp. 325-329. Elsevier Science Ireland Ltd. XP-002569022.
Kawashima, Y. "Molecular alterations of decorin in photoaging process". Fragrance Journal. 2006, vol. 34, No. 12, pp. 53-57. Maruzen Pharmaceuticals, Co., Ltd., Japan. XP-002569023.
Ma'Or, Z., et al. "Skin smoothing effects of Dead Sea minerals: comparative profilometric evaluation of skin surface". International Journal of Cosmetic Science. 1997, vol. 19, pp. 105-110. XP-002257163.
WPI/Derwent. "External use agent for removing freckles and spots from skin—comprises kojic acid (deriv.) and one or more plant extracts, e.g. from Iceland moss, orris root, oak bark, gardenia, mallow, avens, citrus unshiu peel, grape, cornflower, etc.". 1995, vol. 14, No. 95. Sansei Seiyaku KK. XP-002045141.
Third Party Submission under 37 CFR 1.99 in respect of U.S. Appl. No. 12/574,159 and Patent Publication No. 20100111878, filed on Oct. 6, 2009 and published on May 6, 2010; submitted to the USPTO on Jun. 22, 2010, 24 pages total.
Mohammad Azam Khan; Muheet-e-Azam, vol. I (19th century AD), Matba Nizami, Kanpur, 1896 AD., reference page No. of book: 186, with english translation from persian.
Mohammad Najmul Ghani Khan; Khazaain-al-Advia, vol. II (20th century AD), Nadeem Yunus Printer / Sheikh Mohd Basheer & Sons, Lahore, 1911 AD., reference page No. of book: 351, with english translation from urdu.
Mohammad Najmul Ghani Khan; Qaraabaadeen Najm-al-Ghani (20th century AD), Munshi Nawal Kishore, Lucknow, (Second Edition) 1928 AD., reference page No. of book: 785, with english translation from urdu.
Abu Bakr Mohammad Bin Zakariyya Al-Razi; Kitaab-al-Haawi-fil-Tibb, vol. XI (9th century AD), Dayerah-al-Ma'aarif Usmania, Hyderabad, (First Edition) 1962 AD, reference page No. of book: 138, with english translation from arabic.
Suśruta; Suśruta Samhitā—Edited & translated by P.V Sharma, vol. II : Chaukhamba Visvabharati, Varanasi, Edn. 1st, 2000. [Time of origin 1000 BC—5th century], reference page No. of book: 362 with english translation from sanskrit.
Govinda Dāsa; Bhaisajya Ratnāval T—Edited by Rajeshvaradutta Shastri, Translated by Ambikaduttashastri : Chaukhamba Sanskrit Sanskrit Sansthan, Varanasi, Edn. 14th, 2001. [This book contains back references from 1000 B.C. to 18th century], reference page No. of book: 587 with english translation from sanskrit.
Cakrapānidattah; Cakradattah—Translated by Indradeva Tripathi; Chaukhamba Sanskrit Samsthan (Varanasi), Ed. 4th 2002, reference page No. of book: 283-284 with english translation from sanskrit.
European Search Report, dated Feb. 17, 2010.

* cited by examiner

*Primary Examiner* — James H Alstrum Acevedo
*Assistant Examiner* — Daniel L Branson
(74) *Attorney, Agent, or Firm* — Vorys, Sater, Seymour and Pease LLP; Susanne M. Hopkins

(57) ABSTRACT

Composition of a Dead Sea extract and at least one plant extract of a Himalayan origin are provided for topical applications.

18 Claims, 1 Drawing Sheet

SKIN-CARE COMPOSITIONS AND USES THEREOF

This is a Non-Provisional Application, filed Oct. 6, 2009, an application claiming the benefit under 35 U.S.C. 119(e) U.S. Provisional Application No. 61/136,834, filed Oct. 7, 2008, the entire content of which is hereby incorporated by reference in its entirety.

FIELD OF THE INVENTION

This invention relates to compositions useful for skin care and skin protection.

BACKGROUND OF THE INVENTION

Therapeutic and to some extent even cosmetic skin formulations are aimed at replenishing skin moisture; protecting against on-going loss of moisture; removing dead skin cells; decreasing irritation; minimizing irritant release; and minimizing skin conditions associated with e.g., inflammation are among the most sought after formulations. The inclusion of extracts isolated directly from plants and other natural sources or the replacement of synthetic medicaments traditionally used for such purposes by such natural extracts has been proposed not only for reducing undesired toxicity but also for attracting the end user to such greener formulations.

REFERENCES

[1] Cao, G., C. P. Verdon, A. H. Wu, H. Wang, and R. L. Prior. 1995. Automated assay of oxygen radical absorbance capacity with the COBAS FARA II. *Clin Chem* 41:1738-1744.
[2] Prior, R. L., H. Hoang, L. Gu, X. Wu, M. Bacchiocca, L. Howard, M. Hampsch-Woodill, D. Huang, B. Ou, and R. Jacob. 2003. Assays for hydrophilic and lipophilic antioxidant capacity (oxygen radical absorbance capacity (ORAC (FL))) of plasma and other biological and food samples. *J Agric Food Chem* 51:3273-3279.

SUMMARY OF THE INVENTION

Plant extracts have been traditionally obtained from the leaves, stems, flowers and reproductive structures of plants. Outside of the plant, exposed to oxygen and sunlight and in the absence of natural antioxidants and free radical quenching mechanisms, which are typically present in the plant, some of these extracts are more prone to decomposition and other processes which may strip them off their natural attributes and at times even endow them with undesired characteristics and even toxicity. It is for these reasons, amongst others, that natural extracts have typically been provided in inert solutions, in most cases water free, and in dark bottles.

The inventors of the present invention have developed an active and surprisingly stable combination of natural extracts originating from the lowest and one of the most saltiest bodies of water on earth, the Dead Sea, and the highest of places on earth, the Himalaya Range.

As the present application will further disclose, the combination comprising a natural salt-concentrated extract from the Dead Sea and a natural plant extract from the Himalayas has proven not only to be stable but also to have a multitude of skin care and therapeutic attributes, particularly skin related, both protective/preventive and therapeutic.

Thus, the present invention provides in one of its aspects, a composition comprising (i.e., as an active combination) at least one Dead Sea extract and at least one extract (plant extract) selected from an extract of the Himalayan Raspberry (*Rubus ellipticus*), an extract of the Goji Berry (*Lycium Barbarum*) and an extract of the Iceland moss (*Cetraria islandica*).

As used herein, the expression "active combination" refers to the ability of the combination to exert a protective/preventive skin-care/therapeutic effect, as disclosed herein. Neither of the components is regarded as a carrier, diluent or excipient.

In some embodiments, the composition comprises at least one Dead Sea extract and an extract of the Himalayan Raspberry (*Rubus ellipticus*).

In some other embodiments, the composition comprises at least one Dead Sea extract and an extract of the Himalayan Raspberry (*Rubus ellipticus*), an extract of the Goji Berry (*Lycium Barbarum*) and an extract of the Iceland moss (*Cetraria islandica*) (namely a combination of the Dead Sea extract and each of the three plant extracts).

The Dead Sea extract is one or more natural material, in the form of a single material (e.g., inorganic, organic, salt, etc) or a mixture of natural materials obtained from the waters of the Dead Sea, the mud surrounding the Dead Sea and/or the soil bed of the Dead Sea.

In some embodiments, the Dead Sea extract is the Dead Sea water (Maris Sal), which may be obtained directly from the Dead Sea, filtered water substantially having the same salt content (a hypersaline concentration) as that of the unfiltered Dead Sea water, or Dead Sea water treated by any one or more of various other methods employed to e.g., remove organic matter and residual contaminants therefrom.

In some embodiments, the Dead Sea water is a clear colorless viscous liquid (at 25° C.) having:
1. a specific density of 1.25-1.35 g/ml,
2. pH=4.6-5.6 (at 25° C.), and/or
3. less than 100 cfu/g of non-pathogenic microbes.

The Dead Sea water having the above physical characteristics is a concentrated extract of Dead Sea water comprising (among other metal salt ions) $Ca^{+2}$, $Cl^-$, $Mg^{+2}$, $Na^+$, $K^+$ and $Br^-$. In some embodiments, the concentrations of these metal ions are, as assessed by a water analysis carried out by the Geological Survey of Israel:
Calcium ($Ca^{+2}$): 35,000-40,000 mg/L
Chloride (Cr): 320,000-370,000 mg/L
Magnesium ($Mg^{+2}$): 92,000-95,000 mg/L
Sodium ($Na^+$): 1800-3200 mg/L
Potassium ($K^+$): 2,500 mg/L, and
Bromide (Br): 10,000-12,000 mg/L.
Other minerals may also exist in the waters, e.g., at much lower concentrations.

Thus, in some embodiments, the Dead Sea water (herein referred to as Dead Sea water I) comprises:
Calcium ($Ca^{+2}$): 35,000-40,000 mg/L
Chloride (Cr): 320,000-370,000 mg/L
Magnesium ($Mg^{+2}$): 92,000-95,000 mg/L
Sodium ($Na^+$): 2400-3200 mg/L
Potassium ($K^+$): 2,500 mg/L, and
Bromide (Br): 10,000-12,000 mg/L.

In other embodiments, the Dead Sea water (herein referred to as Dead Sea water II) comprises:
Calcium ($Ca^{+2}$): 5,000-10,000 mg/L
Chloride ($Cl^-$): 315,000-360,000 mg/L
Magnesium ($Mg^{+2}$): 100,000-150,000 mg/L
Sodium ($Na^+$): 1800-2200 mg/L
Potassium ($K^+$): 1,000-2,000 mg/L, and
Bromide ($Br^-$): 5,000-10,000 mg/L.

In some other embodiments, the Dead Sea component is Dead Sea mud.

The term "extract" is used herein in its broadest definition. The term relates to a fraction obtained from the Dead Sea, e.g., water, mud, etc., or from one or more parts (e.g., roots, leaves, stems, fruits and/or flowers) of a plant, e.g., Himalayan Raspberry, Goji Berry, and Iceland moss. The extract is typically an active fraction having by itself at least one attribute which may be enhanced in a combination according to the invention. The extract from the Himalayan Raspberry, Goji Berry, or Iceland moss is an extract obtained according to known procedures or a commercially available extract, as disclosed. The extract may be a pure (neat) extract or an extract formulated along with a predetermined amount of an additive such as a stabilizer, diluent, carrier, filler, antioxidant or any other inert additive.

The at least one plant extract employed in the composition of the invention is an extract of the Himalayan Raspberry, Goji Berry and Iceland moss, originating from the high Himalayan mountains. For purposes herein, the plants from which the extracts are obtained may be those native to the Himalayan Mountains or otherwise grown outside of this region, naturally, e.g., due to natural invasion, or for commercial purposes, horticulture purposes or for any other reason.

The Himalayan Raspberry (*Rubus ellipticus*) is a stout evergreen shrub with stems about 12 feet long. Its thick leaves are about 3-4 inches long and 2-3 inches wide, divided into three roughly equal "finglers" with toothed leaf margins and inch-long leaf stalks that are densely covered with prickles. The flowers of Himalayan Raspberry are white and occur in short, terminal panicles. The extract from the Himalayan Raspberry is obtained by extracting the root parts of the plant in alcohol (e.g., 80% ethanol) to obtain a light brown to brown liquid with a specific gravity of 1-1.1 and pH=3-5.

The extract may also be obtained commercially from various sources. In some embodiments, the extract is Extract BG80, obtained from Maruzen Pharmaceutical Co., LTD Japan, as a formulation comprising 79.2% 1,3-butyleneglycol, 19.8% water (purified) and 1% of the root extract 1%. Another commercially available Himalayan Raspberry extract is that sold under Himalayan Raspberry Root BG by Barnet Products Corporation.

The Goji Berries (*Lycium Barbarum*) extract is obtained from the fruits, for example, by mixing the fresh or dried berries into cold or hot aqueous or organic solvent. The extract thus obtained is a light to medium yellow liquid with a specific gravity of 1.05-1.15 (at 25° C.) and pH=4.0-6.5 (at 25° C.).

The extract may be obtained commercially. One such commercially available extract—the Actiphyte of Goji Berries GL by Active Organics, LP., USA, was used in some of the examples provided herein, in the form of a formulation comprising 79% glycerin, 20% of the fruit extract and 1% preservative.

The Iceland Moss (*Cetraria islandica*) is an erect lichen which appearance resembles that of a moss. As with all other lichens, the Iceland Moss is a composite organism formed from two distinct types of plants, one is a species of fungus and one is a species of alga. The extract of the Iceland Moss is obtained, in accordance with some extraction methods, by boiling the whole plant in water or an organic solvent, typically an alcohol. The extract thus obtained is a liquid light to pale yellow in color with a specific gravity of 1.02-1.05 (at 25° C.) and pH=4.0-6.5 (at 25° C.).

The extract may be obtained commercially. One such commercially available extract is the Actiphyte of Iceland Moss GL by Active Organics, LP. USA, was used in some of the examples provided herein, in the form of a formulation comprising 79% Glycerin, 20% moss extract and 1% preservative.

In some embodiments, the composition of the invention may further comprise at least one plant extract selected from *Aesculus Hippocastanum* (horsechestnut), *Ruscus Aculeatus* (butcherbroom), *Acer Saccharinum* (sugar maple), *Citrus Aurantium Dulcis* (orange), *Citrus Medica Limonum* (lemon), *Saccharum Officinarum* (sugar cane), *Vaccinium Myrtillus* (bilberry), *Equisetum Arvense* (horsetail), *Siegesbeckia Orientalis*, *Rabdosia Rubescens*, *Chamomilla Recutita* (matricaria), *Centella Asiatica*, *Calendula Officinalis*, *Pichia*\Resveratrol Ferment, *Rosa Centifolia*, *Dunaliella Salina*, *Phoenix Dactylifera* (date) and any combination thereof.

In some embodiments, the composition of the invention further comprises at least one plant extract selected from *Dunaliella Salina* extract, *Phoenix Dactylifera* (date) fruit extract and any combination thereof.

In some embodiments, the composition of the invention is a cosmetic composition. In other embodiments, the composition is a pharmaceutical composition. In further embodiments, the pharmaceutical composition is for topical application.

In further embodiments, the composition is a synergistic composition.

The compositions of the present invention may be made into a wide variety of product forms suitable for, e.g., topical administration onto the skin of a subject. Non-limiting examples are a lotion, an ointment, a gel, a shampoo, a moisturizer, a sunscreen, a cream, a stick, a spray, an aerosol, foam, a paste, a mousse and a variety of cosmetics or skincare formulations including solid, semi-solid, or a liquid make-up such as foundations, eye make-up, etc. In some embodiments, the composition of the invention is formulated as a lotion.

In some embodiments, the formulated compositions of the invention are those referred herein as Formulations 1 to 4, or any equivalent according to the invention.

The viscosity of the composition may vary depending on the form (i.e., lotion, cream, etc), concentration of the active combination, the carrier, the purpose (i.e., cosmetic or therapeutic), end user and other parameters.

The compositions according to the invention (cosmetic or therapeutic) may comprise at least one dermatological, cosmetically or pharmaceutically acceptable additive selected amongst inert and effect-inducing additives. In some embodiments, the inert additive is selected from a diluent, a preservative, an abrasive, an anti-caking agent, an antistatic agent [e.g., panthenol (Pro vitamin B5)], a binder, a buffer (e.g., citric acid), a dispersant, an emollient, an emulsifier, a co-emulsifiers, a fibrous material, a film forming agent, a fixative, a foaming agent, a foam stabilizer, a foam booster, a gellant a lubricant, a moisture barrier agent, an opacifier (e.g., styrene/acrylamide copolymer), a plasticizer, a preservative, a propellant, a stabilizer a surfactant, a suspending agent, a thickener, a wetting agent, and a liquefier.

In some embodiments, the at least one inert additive is a smoothness enhancer ingredient, such as silica.

Each of the at least one dermatological, cosmetically or pharmaceutically acceptable additives may constitute between about 0.05 to 15% of the total weight of the formulation. In some embodiments, the at least one additive constitutes between 0.05% and 10% or between 0.05% and 8%, or between 0.05% and 7%, or between 0.05% and 6%, or between 0.05% and 5% of the total weight of the formulation.

In some embodiments, the at least one inert additive is a diluent being selected from water, bisabolol, propane diol, propylene glycol, butylene glycol, glycerin, safflower oil and mixtures thereof.

In other embodiments, the at least one inert additive is a preservative being selected from methylparaben, methyldibromo glutaronitrile, phenethyl alcohol, glyceryl caprilate, propylparaben, methylisothiazolinone, decylene glycol, dehydroacetic acid, phenoxyethanol, benzoic acid, 2-methyl-2H-isothiazoline-3-one, polyethylene glycol monococoate, polyethylene glycol dicocoate, polyethylene Glycol, iodopropynyl butylcarbamate, 1.2-hexanediol, caprylyl glycol, imidazolidinyl urea, DMDM Hydantoin, Ipbc, MIT, 2,3-bronopol, and any combination thereof.

In further embodiments, the inert additive is an emulsifier being selected from cetyl hydroxyethylcellulose, cetyl alcohol, ceteth-20 (a polyethylene glycol derivative of cetyl alcohol), cetearyl olivate, cetyl palmitate, sorbitan olivate, sorbitan palmitate, stearates, steareth-20 (polyethylene glycol ethers of stearic acid—octadecyl polyoxyethylene ether), steareth-25 and mixtures thereof.

In some embodiments, the stearate is selected from PEG-40 stearate, glyceryl steatrate, sorbitan tristearate, stearyl alcohol and mixtures thereof. In some embodiments, the stearate is glyceryl stearate. In still other embodiments, the inert additive is an emollient, being selected from vegetable and animal fats and oils such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (matricaria) flower oil, hypericum perforatum oil, soybean oil and vitis vinifera (grape) seed oil; acetoglyceride esters, such as acetylated monoglycerides; alkyl esters of fatty acids having 10 to 24 carbon atoms which include, but are not limited to, methyl, isopropyl, and butyl esters of fatty acids such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; vegetable waxes including, but not limited to, carnauba and candelilla waxes; surface active silicone derivatives such as cyclopentasiloxane PEG/PPG-18/18 dimethicone, dimethicone, dimethicone crosspolymer, cyclomethicone, cyclomethicone&dimethiconol; caprylic/capric triglyceride; and cholesterol fatty acid esters and any mixtures thereof.

Each of the at least one inert additive may constitute between about 0.05 to 15% of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

In other embodiments, the effect-inducing additive is selected from an anti-acne agent, an anti-aging agent, an antibacterial agent, an anti-cellulites agent, an antidandruff agent, an antifungal agent, an anti-inflammatory agent, an anti-irritation agent (e.g., allantoin, Aloe Barbadensis leaf juice), an antimicrobial agent, an antioxidant (e.g., butylated hydroxyanisole, propyl gallate, an antiperspirant agent, an antiseptic agent, a cell stimulant, a cleansing agent, a conditioner, a deodorant, a fragrance ingredient (e.g., perfume, limonene), a depilatory, a detergent, an enzyme, an essential oil, an exfoliant, a fungicide, a glosser, hair conditioner (hair conditioner agent), hair set resin, hair sheen agent, hair waving agent, a humectants (e.g., Erythritol, Homarine HCl, *Ceratonia Siliqua* (carob bean) gum), a moisturizer (e.g., sodium hyaluronate), an ointment base, a perfume, a protein, a skin calming agent, a skin cleanser, a skin conditioner (skin conditioning agent), a skin healing agent, a skin lightening agent, a skin protectant, a skin smoothing agent, a skin softening agent, a skin soothing agent, a sunscreen agent, a tanning accelerator, vitamins, a colorant, and a flavoring agent.

In some embodiments, the effect-inducing additive is an oligopeptide of a short chain of 2 to 7 amino acids. The oligopeptide may be connected to palmitic acid. Non limiting examples include palmitoyl oligopeptide (Pal-GHK) and palmitoyl tetrapeptide-3, a peptide of amino acids valine and tryptophan (Dipeptide-2).

In some embodiments, the at least one additive is a sunscreen, such as octyl methoxycinnamate.

Each of the at least one effect-inducing additive may constitute between about 0.05 to 15% of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

The cosmetic or pharmaceutical compositions of the invention may also comprise pharmaceutical actives useful in the form of a chemical substance, material or compound, e.g., suitable for topical administration, to induce a desired local or systemic effect. Non-limiting examples of such actives are an antibiotic, an antiviral agent, an analgesic (e.g. ibuprofen, acetyl salicylic acid, naproxen, and the like), an antihistamine, an anti-inflammatory agent, an antipruritic, an antipyretic, an anesthetic agent, a diagnostic agent, a hormone, an antifungal agent, an antimicrobial agent, a cutaneous growth enhancer, a pigment modulator, an antiproliferative, an antipsoriatic, a retinoid, an anti-acne medicament (e.g. benzoyl peroxide, sulfur, and the like), an antineoplastic agent, a phototherapeutic agent, a keratolys (e.g. resorcinol, salicylic acid, and the like) and mixtures thereof.

In some further embodiments, the composition of the invention also comprises deep seawater. As used herein, "deep seawater" refers to water drawn from deep in the ocean, for example in a region of the ocean off the Hawaiian shores, usually 2,000 to 3,000 feet below water surface. Water at such a depth is free of the contaminants and pollutants. Deep seawater is also pathogen free and naturally rich in important nutrients and minerals.

The deep seawater employed in the compositions of the present invention comprises:

$NO_3/NO_2$ concentration between 0.2-39.0 μM/L,
$PO_4$ concentration between 0.1-3 μM/L,
Si concentration between 2.6-75 μM/L,
$NH_4$ concentration between 0.05-0.2 μM/L,
Dissolved organic nitrogen concentration between 5-42 μM/L,
Dissolved oxygen concentration between 1.2-6.9 μM/L,
Total organic carbon concentration between 0.5-0.7 μM/L, and
Total suspended solid concentration between 0.3-0.9 μM/L.

Additionally, the deep seawater has:
Salinity between 34-35%,
pH between 7.6-8.3, and
Alkalinity between 2.31-2.36.

Application of a composition of the invention onto the skin of a subject, for cosmetic/skin-care or therapeutic purposes may be in a single dose, in multiple doses, in a continuous or intermittent manner, depending, for example, upon the subject's physiological condition, whether the purpose of the administration is cosmetic or therapeutic/prophylactic and other factors known to the medical practitioner. The application of a composition of the invention may be essentially continuous over a pre-selected period of time or may be in a series of spaced doses.

The compositions of the invention are typically prepared by combining the ingredients of the active combination in appropriate concentrations. Other active or inert additives selected by one of skill in the art can optionally be added. The absolute weight of a given active agent included in a unit dose can vary widely. For example, about 0.1 microgram to about 5 g, or about 1 microgram to about 1 g, or about 10 microgram to about 500 mg, of at least one of the components can be administered by topical administration.

The compositions of the invention, being substantially for topical use, may be a skin-care formulation or a therapeutic formulation.

In some embodiments, the compositions of the invention are skin-care or dermo-pharmaceutical compositions (including, e.g., toiletries, health and beauty aids and cosmeceuticals) used for cosmetic and personal skin-care applications. The term "cosmetic composition" or "skin care composition" relates to a composition of the invention that can be used for cosmetic purposes, purposes of hygiene or skin-care or as a basis for delivery of one or more pharmaceutical ingredients. It is also possible that these compositions are used for two or more of these same purposes at one time. For example, a medicated dandruff shampoo may be used as a personal care product, i.e., to provide clean hair, and at the same time have pharmacological properties.

In some embodiments, the cosmetic compositions are for promoting bodily attractiveness, cover or mask the physical manifestations of a disorder or disease, modulate or alleviate wrinkling, photo-damage, unevenness and dryness in the skin of a mammal. The compositions additionally regulate skin condition and signs of skin aging (all perceptible manifestations as well as any other macro or micro effects) by regulating visible and/or tactile discontinuities in skin texture, including fine lines, wrinkles, enlarged pores, roughness and other skin texture discontinuities associated with aged skin with reduced irritation and dryness.

Thus, the invention further provides a method of protecting and/or improving the state of the skin, preventing and/or treating imperfections of the skin of a subject in need thereof, said method comprising topically administering a composition according to the invention onto the skin of said subject.

In some embodiments, said method is used for treating rings under the eye, symptoms of aging, protecting the skin, increasing the detoxification of xenobiotics, intervening on pigmentation level, inhibiting melanogenesis, protecting the body against pollution, stimulating the detoxification systems, stimulating hair and body hair growth, modulating DHT levels, intervening on adipocytes, and promoting lipolysis.

In other embodiments, the compositions are pharmaceutical composition used in the treatment or prevention of at least one disease or disorder, e.g., of the skin.

In another aspect of the present invention, there is provided a use of at least one Dead Sea extract and at least one plant extract selected from Himalayan Raspberry, Goji Berry, and Iceland moss for the preparation of a composition.

In some embodiments, the use is for the preparation of a composition comprising a Dead Sea extract and an extract of the Himalayan Raspberry.

In other embodiments, the use is for the preparation of a composition comprising a combination of at least one Dead Sea extract and a Himalayan Raspberry extract, a Goji Berry extract and an Iceland Moss extract.

The compositions of the invention, in some embodiments, are formulated for use in the treatment of a disease or disorder, e.g., of the skin. Thus, the present invention also provides a method of therapeutic treatment or prophylaxis of such skin related disease or disorder.

In a further aspect, there is provided a method for treating a disease or disorder of the skin, said method comprising administering to a subject in need thereof a composition according to the invention.

In some embodiments, the subject is suffering, or has predisposition to suffer, or is one which may be exposed to conditions which increase the chances of suffering from a disease or disorder of the skin, which is optionally (may or may not be) related to one or more of age, sex, skin color, skin wounds, exposure to the sun, UV radiation, inflammation, a pre-existence of a disease not associated with the skin, etc.

In some embodiments, the disease or disorder of the skin is related to sun exposure.

In other embodiments, the disease or disorder of the skin is a secondary condition, e.g., inflammation, being related to an existing condition.

In further embodiments, the disease or disorder of the skin are age-related.

Non-limiting examples of such diseases or disorders of the skin are wounds, acne, psoriasis, atopic skin, diabetic skin, dermatitis, eczema, xerotic, dry skin, and chaffed skin.

In some embodiments, said administration is topical.

The term "topical" as used herein refers to the application of a composition according to the invention directly onto at least a portion of a subject's skin (human's or non-human's skin) so as to achieve a desired effect, e.g., cosmetic or therapeutic effect, at the site of application. In some embodiments, the desired effect is achieved at the site of application without inducing one or more systemic effects. In other embodiments, the formulation of the invention induces at least a partial systemic effect which contributes to the induction of at least one desired effect.

The term "skin" as used herein refers to any part of the human or animal skin, including the whole surface thereof, hair and nails.

The term "treatment" as used herein refers to the topical administration of an effective amount of a composition of the present invention effective to ameliorate undesired symptoms associated with a skin disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

The "effective amount", whether a therapeutically or cosmetically effective amount for purposes herein, is determined by such considerations as may be known in the art. The amount must be effective to achieve one or more of the above desired therapeutic or cosmetic effects, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile, a variety of pharmacological parameters such as half life on the skin, on undesired side effects, if any, on factors such as age and gender, etc.

A method is also provided, for protecting the skin of a subject from UV-induced disease or disorder, said method comprising applying to the skin of said subject a composition according to the invention.

In some embodiments, the UV-induced disease or disorder is apoptosis or inflammation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

As used herein, the singular form "a", "an" and "the" include plural references unless the context clearly dictates otherwise. For example, the term "an extract" or "at least one extract" may independently include a plurality of extracts, including a variety thereof.

Various embodiments and aspects of the present invention as delineated hereinabove and as claimed in the claims section below find experimental support in the following examples.

BRIEF DESCRIPTION OF THE FIGURES

In order to understand the invention and to see how it may be carried out in practice, embodiments will now be described, by way of non-limiting example only, with reference to the accompanying drawings, in which.

DETAILED DESCRIPTION OF THE INVENTION

Figure 1:
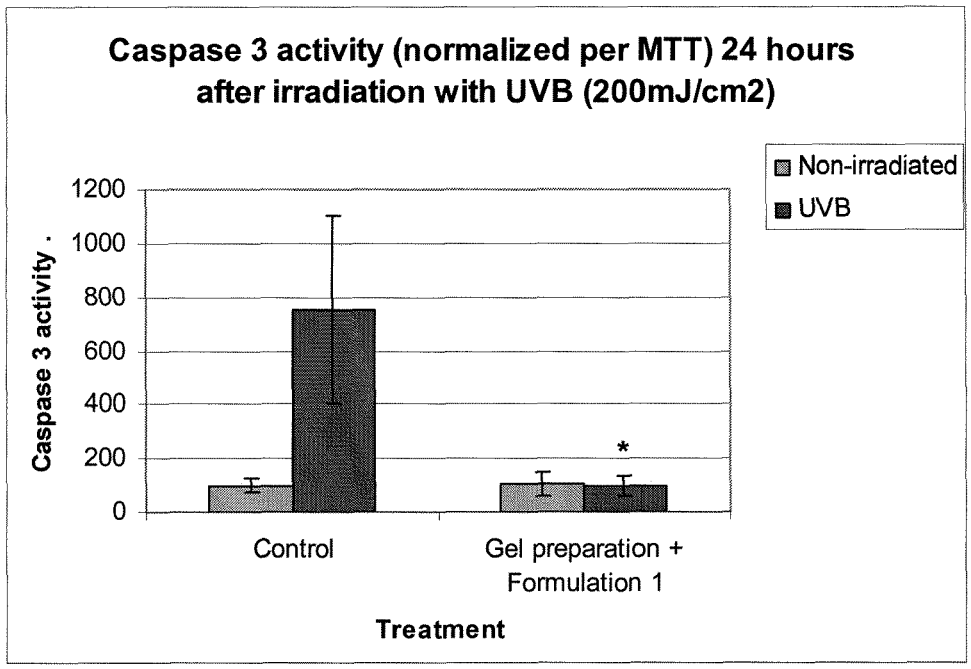
FIG. 1 demonstrates the Caspase 3 activity (normalized per MTT) 24 hours after irradiation with UV-B.

The following examples are not in any way intended to limit the scope of the inventions as claimed.

EXAMPLE 1

Formulations

Formulation 1—This formulation according to the invention was prepared by mixing.

50% w/w Dead Sea water,

25% w/w Actiphyte of Iceland Moss (in the form of a formulation), 12.5% w/w Himalayan Raspberry root extract BG80 (in the form of a formulation), and 12.5% w/w Actiphyte of Goji Berries GL (in the form of a formulation).

The content of the active combination in this formulation was 50% Dead Sea water, 5% *Cetraria islandica*, 2.5% *Lycium Barbarum* and 0.125% *Rubus ellipticus* (w/w).

In this formulation, the Dead Sea water (Dead Sea water I) comprised:

Calcium ($Ca^{+2}$): 35,000-40,000 mg/L

Chloride ($Cl^-$): 320,000-370,000 mg/L

Magnesium ($Mg^{+2}$): 92,000-95,000 mg/L

Potassium ($K^+$): 2,500 mg/L, and

Bromide ($Br^-$): 10,000-12,000 mg/L.

Formulation 2—This formulation according to the invention was prepared as above with the Dead Sea water (Dead Sea water II) comprising:

Calcium ($Ca^{+2}$): 5,000-10,000 mg/L

Chloride ($Cl^-$): 315,000-360,000 mg/L

Magnesium ($Mg^{+2}$): 100,000-150,000 mg/L

Potassium ($K^+$): 1,000-2,000 mg/L, and

Bromide ($Br^-$): 5,000-10,000 mg/L.

Formulation 3—This formulation according to the invention was prepared by mixing:

50% w/w deep seawater

25% w/w Dead Sea water (Dead Sea water I), 12.5% w/w Actiphyte of Iceland Moss (in the form of a formulation), 6.25% w/w Himalayan Raspberry root extract BG80 (in the form of a formulation), and 6.25% w/w Actiphyte of Goji Berries GL (in the form of a formulation).

The content of the active combination in this formulation was 50% Deep Sea water 25% Dead Sea water, 2.5% *Cetraria islandica*, 1.25% *Lycium Barbarum* and 0.0625% *Rubus ellipticus* (w/w).

Formulation 4—This formulation according to the invention was prepared similarly to Formulation 3 with Dead Sea water II.

EXAMPLE 2

Topical Preparations

The formulations of the invention were made into topical preparations, e.g., gels, lotions, creams, ointments, soaps etc, by employing preparation methodologies known in the art. Table 1 below exemplifies 4 different topical preparations, wherein the Base is the additive material (e.g., carrier, diluent, preservative, etc), Dead Sea water I and II and deep seawater are as defined hereinabove.

B. Oil in Water Emulsion

Oil in water (o/w) emulsion was prepared by first mixing phase 1: 67-70% water, 0.3-0.4% methyl paraben, 0.2-0.3% imidazolylidinyl urea, 0.07-0.08% allantoin, 2.6-2.8% glycerin, 0.9-1% propylene glycol and 2.8-3% sodium ceteapyl sulfate at a temperature between 75-80° C. In a different container maintained at 75-80° C., a mixture was prepared of phase 2: 4.3-4.5% cetearyl alcohol ceteareth-30, 3.3-3.5% cetyl alcohol C-16, 0.1-0.2% propyl paraben, 0.4-0.5% dimethicone 350, 9-9.5% octyl palmitate and 0.1-0.2% butyl paraben.

In the next stage, while holding the temperature, phase 2 was added into phase 1 and the mixing was maintained, e.g., by an agitator. After combining the phases, the resulting emulsion was transferred to allow homogenization until the temperature cooled to about 60° C. and than mixing was initiated again. At 35-40° C., 0.04-0.05% bronopol, 0.004-0.005% lactic acid and 4% of Formulation 1 or Formulation 2 or 8% of Formulation 3 or Formulation 4 were added while mixing.

The stability and characteristics of the preparations of 4 formulations is summarized in Table 2 below.

TABLE 2

Stability and characteristics of o/w preparations of Example 2B, for Formulations 1 to 4.

| Preparation No. | Odor | | Color | | Stability - Viscosity measurements | | pH |
|---|---|---|---|---|---|---|---|
| | Time 0 | After 1 month 45° C. | Time 0 | After 1 month 45° c. | Time 0 | After 1 month 45° c. | |
| I | None | None | white | white | Homogeneous solution 2.5 rpm-100,000 cps 5 rpm-57,400 cps | Stable | 5 |
| II | None | None | white | white | Homogeneous solution 2.5 rpm-92,000 cps 5 rpm-49,200 cps | Stable | 3.5 |
| III | None | None | white | white | Homogeneous solution 2.5 rpm-100,000 cps 5 rpm-52,000 cps | Stable | 5.2 |
| IV | None | None | white | white | Homogeneous solution 2.5 rpm-112,000 cps 5 rpm-58,400 cps | Stable | 3.5 |
| Control (cream alone) | None | None | white | white | Homogeneous solution 2.5 rpm-148,000 cps 5 rpm-84,000 cps | Stable | 5.7 |

Viscosity (cps) was measured on a Brookfield digital viscometer model DV-I Needle C; pH was measured on a HANNA instrument HI 8521.

TABLE 1

Topical preparations

| Preparation No. | % Carrier | % Formulation |
|---|---|---|
| I | 96% | Formulation 1 - 4% |
| II | 96% | Formulation 2 - 4% |
| III | 92% | Formulation 3 - 8% |
| IV | 92% | Formulation 4 - 8% |

A. Gel Preparation

A gellous formulation was prepared by first preparing the carrier gel by mixing w/w 98.5% water, 1% guar hydroxypropyl triammonium chloride and 0.5% citric acid (50% in water). The carrier gel was then mixed manually at room temperature with the active combination comprising w/w 94.56% water, 0.96% guar hydroxypropyl triammonium chloride, 0.48% citric acid (50% in water) and 4% of a formulation of the invention such as that of Example 1.

C. Water in Oil Emulsions

A water in oil (w/o) emulsion was prepared by first mixing phase 1: 58.6-61.2% water, 3.3-3.5% glycerin and 4% of Formulation 2 or 8% of Formulation 3 according to the invention, at room temperature.

In a separate container were mixed phase 2: 0.48-0.5% cetyl PEG/PPG-10/1Dimethicon, 2.4-2.5% caprylic/capric triglyceride/stearalkonium hectorite/propylene carbonate, 3-3.2% cyclomethicone, 9.6-10% cyclomethicone and dimethicone copolyol, 9.3-9.7% cyclopentasiloxane/dimethicone cross polymer, 3.8-4% isostearyl isostearate, 0.48-0.5% polyglyceryl-4 isostearate, 0.09-0.1% iodopropynyl butylcarbamate and 0.07-0.8% ethyl paraben.

Then, phase 1 was added to phase 2, mixed and homogenized for 5 minutes.

The stability and characteristics of preparations of 2 different formulations of the invention are summarized in Table 3 below.

TABLE 3

Stability and characteristics of w/o preparations
of Example 2C, for Formulations 2 and 3.

| Preparation No. | Odor | | Color | | Stability Viscosity measurements | |
|---|---|---|---|---|---|---|
| | Time 0 | After 1 month 45° c. | Time 0 | After 1 month 45° c. | Time 0 | After 1 month 45° c. |
| II | None | None | white | white | Homogeneous solution 2.5 rpm-22,560 cps 5 rpm-12,880 cps | Stable |
| III | None | None | white | white | Homogeneous solution 2.5 rpm-22,400 cps 5 rpm-13,200 cps | Stable |

Viscosity was measured on a Brookfield digital viscometer model DV-I Needle C.

D. Sunscreen Preparations

An emulsion was prepared by first mixing phase 1: 50.25% water, 3.4% propandiol 1,3, 0.2% allantoin, 0.5% natrosol hydroxyethylcellulose, 1% glycerin and 0.3% chlorophenesin, at a temperature between 75-80° C.

In a separate container at a temperature between 75-80° C., were mixed phase 2: 1.1% PEG-40 stearate, 2.5% cetyl alcohol C-16, 4.4% glyceryl stearate/PEG-100 stearate, 1.1% sorbitan tristearate, 10% octyl palmitate, 0.8% phytosqualan, 1.5% C-12-15 alkyl benzoate, 7% isohexadecane, 7.5% octyl methoxy cinnamate, 0.05% BHA and 2.8% titanium oxide.

While holding the temperature at this level, phase 2 was added into phase 1 and mixing was continued e.g., by an agitator. Thereafter, the resulting emulsion was transferred to a homogenizer and the temperature was allowed to drop to 60° C., before it was transferred to an agitator again. At 35-40° C., to the emulsion were added 1.4% dimethicone and dimethiconol, 0.1% iodopropynyl butylcarbamate, 0.1% methylisothiazolinone and 4% of a Formulation of the invention.

The stability of a preparation made of Formulation 1 is summarized in Table 4 below.

TABLE 4

Stability and characteristics of SPF preparations
of Example 2D, for Formulation 1.

| | Stability Viscosity measurements - | | pH measure- |
|---|---|---|---|
| | Time 0 | After 1 month 45° C. | ments- |
| Preparation I | Homogeneous solution 2.5 rpn-35,840 cps 5 rpm-26,080 cps | Homogeneous solution 2.5 rpm-42,880 cps 5 rpm-24,800 cps | 5.88 |
| cream alone (control) | Homogeneous solution 2.5 rpm-43,680 cps 5 rpm-26,240 cps | Homogeneous solution 2.5 rpm-43,200 cps 5 rpm-25,600 cps | 6.42 |

Viscosity was measured on a Brookfield digital viscometer model DV-I Needle C; pH was measured on a HANNA instrument HI 8521.

E. Soap

Soap was prepared by first mixing 66-69% water and 0.76-0.8% hydroxypropyl guar hydroxypropyltrimonium chloride at room temperature for 15 minutes. Then, 0.38-0.4% *Ricinus Communis* (Castor) seed oil and 0.5-0.6% guar hydroxypropyltrimonium chloride were added and the components were mixed for additional 1 hour. Finally, 0.09-0.1% dipotassium glycyrrhizinate, 14.3-15% magnesium laureth sulfate, 9.5-9.9% cocamido propyl betain, 0.09-0.1% iodopropynyl butylcarbamate, 0.09-0.1% 2-methyl-2H-isothiazolin-3-one, and 4% of Formulation 2 or 8% of Formulation 3 of the present invention were added.

The stability and physical characteristics of the soap are summarized in Table 5 below.

TABLE 5

Stability and characteristics of a soap preparation of Example 2E, for Formulations 2 and 3.

| | Odor | | Color | | Stability | | pH |
|---|---|---|---|---|---|---|---|
| | Time 0 | After 1 month 45° c. | Time 0 | After 1 month 45° c. | Time 0 Viscosity measurements | After 1 month 45° c. | pH measurements- |
| II | None | None | hazy yellowish | hazy yellowish | Homogeneous solution 2.5 rpm-28,640 cps 5 rpm-21,200 cps | stable | 5.81 |
| III | None | None | hazy yellowish | hazy yellowish | Homogeneous solution 2.5 rpm-30,400 cps 5 rpm-21,520 cps | stable | 5.70 |

TABLE 5-continued

Stability and characteristics of a soap preparation of Example 2E, for Formulations 2 and 3.

| | Odor | | Color | | Stability | | pH |
|---|---|---|---|---|---|---|---|
| | Time 0 | After 1 month 45° c. | Time 0 | After 1 month 45° c. | Time 0 Viscosity measurements | After 1 month 45° c. | pH measurements- |
| Control (cream alone) | None | None | hazy | hazy | Homogeneous solution 2.5 rpm-22,720 cps 5 rpm-16,240 cps | stable | 6.12 |

Viscosity was measured on a Brookfield digital viscometer model DV-I Needle C; pH was measured on a HANNA instrument HI 8521.

For other additives and general information regarding the preparation of cosmetic formulations, in addition to those disclosed herein, see for example the Cosmetic Ingredient Dictionary, published by the Cosmetic, Toiletry, and Fragrance Association, Washington D.C., such as can be found in any edition thereof, for example, Volumes 1 and 2, Sixth Edition, (1995) or Volumes 1-3, Seventh and Eighth Editions, (1997, 2000); the 2001 McCutcheon's Directories, Volume 1: Emulsifiers and Detergents and Volume 2: Functional Materials, published by McCutcheon's Division; The Manufacturing Confectioner Publishing Co., Glen Rock, N.J. (2001); and 2001 Cosmetic Bench Reference, edition of COSMETICS and TOILETRIES(R), 115 (13), published by Allured Publishing Corporation, Carol Stream, Ill. (2001); Also, Cosmetics Science and Technology, First Edition (Sagarin (ed)), published 1957, and Second Edition (Balsam, et al. (eds)), published 1972-74; and The Chemistry and Manufacture of Cosmetics, Second Edition (deNavarre (ed)), published 1975, and Third Edition (Schlossman (ed)), published 2000, both available from Allured Publishing Corporation; Rieger (ed), Harry's Cosmeticology, 8th Edition, Chemical Publishing, Co., Inc., New York, N.Y. (2000); and various formularies available to those skilled in the pharmaceutical arts, such as Remington's Pharmaceutical Sciences, Fourteenth Edition, Mack Publishing Company, Easton, Pa. (1970).

EXAMPLE 3

Determination of the Overall Antioxidant Concentrations in Sample Formulations The overall antioxidant concentrations in various samples were determined by using the Oxygen Radical Absorbance Capacity (ORAC) assay [1] adapted to fluorescein (FL) labeling [2].

The ORAC assay measures the oxidative degradation of the fluorescent molecule (either beta-phicoerythrin or fluorescein) after being mixed with free radical generators such as azo-initiator compounds. Azo-initiators are considered to produce peroxyl free radical by heating, which damages the fluorescent molecule, resulting in the loss of fluorescence. Antioxidant is able to protect the fluorescent molecule from the oxidative degeneration. The degree of protection will be quantified using a fluorometer.

The fluorescent intensity decreases as the oxidative degeneration proceeds, and this intensity is recorded for typically 35 minutes after the addition of the azo-initiator (free radical generator). The degeneration (or decomposition) of fluorescein that is measured as the fluorescence delay becomes less prominent by the presence of antioxidants. Decay curves (fluorescence intensity vs. time) are recorded and the area between two decay curves (with or without antioxidant) is calculated. Subsequently, the degree of antioxidant-mediated protection is quantified using the antioxidant trolox (a vitamin E analogue) as a standard. Different concentrations of Trolox are used to make a standard curve, and test samples are compared to this.

Measurements were performed on a Fluostar Galaxy plate reader (BGM, Germany) equilibrated at 37° C., with excitation and emission set up at 485 nm and 520 nm, respectively. 2,2'-Azobis(2-amidino-propane) dihydrochloride (AAPH) (Sigma-Aldrich, Steinheim, Germany) was employed as a peroxyl generator, and Trolox as a calibration standard. All reagents were prepared in 75 mM phosphate buffer (pH 7.4). 40 µl aliquotes of sample, blank or Trolox dilutions were transferred into a 96-well microtiter plate. FL (Sigma-Aldrich, Steinheim, Germany) were added to a final concentration of 96 nM. $ORAC_{FL}$ fluorescence was read every 2 min for 70 min. Peroxyl radical-induced oxidation started immediately after AAPH addition. Results were quantified by comparison with Trolox calibration curves, as above. Total antioxidant capacity was calculated by measuring the area below the kinetic curve.

Results:

As Tables 6 and 7 show, for the formulations of the invention, in comparison to each of its components individually, the experimental ORAC value was higher than the theoretical ORAC value calculated. In fact, the experimental ORAC value for the formulations of the invention was 3.6 times higher than the theoretical ORAC value sum for the same formulation.

TABLE 6

Experiment no. 1

| | Sample 1 | Sample 2 | Sample 3 | Sample 4 | Sample 5 | Form. 1 | Form. 2 |
|---|---|---|---|---|---|---|---|
| Dead Sea water I | 100% | — | — | — | — | 50% | — |
| Dead Sea water II | — | 100% | — | — | — | — | 50% |
| Goji | — | — | 100% | — | — | 12.5% | 12.5% |
| Raspberry | — | — | — | 100% | — | 12.5% | 12.5% |
| Moss | — | — | — | — | 100% | 25% | 25% |
| SUM | 100% | — | 100% | 100% | 100% | 100% | 100% |
| Experimental ORAC value (µM trolox) | 105 | 76 | 2354 | 6309 | 339 | 4418 | 4174 |

TABLE 7

Experiment no. 1

| | Experimental ORAC value (µM trolox) | | Formulation 1 - theoretical ORAC value (µM Trolox) by calculation |
|---|---|---|---|
| Dead Sea water I | 105 | 50% | 52.5 |
| Goji | 2354 | 12.5% | 294.25 |

TABLE 7-continued

Experiment no. 1

| | Experimental ORAC value (µM trolox) | | Formulation 1 - theoretical ORAC value (µM Trolox) by calculation |
|---|---|---|---|
| Raspberry | 6309 | 12.5% | 788.625 |
| Moss | 339 | 25% | 84.75 |
| SUM | | 100% | 1220.125 |

Tables 8 and 9 similarly indicate that the experimental ORAC value for the formulation of the invention was 3.4 times higher than the theoretical ORAC value sum for the same formulation.

TABLE 8

Experiment no. 2

| | Sample 1 | Sample 2 | Sample 3 | Sample 4 | Sample 5 Formulation 1 | Sample 6 | Sample 7 | Sample 8 |
|---|---|---|---|---|---|---|---|---|
| Dead Sea water I | 100% | — | — | — | 50% | 50% | 50% | 50% |
| Goji | — | 100% | — | — | 12.5% | 12.5% | | |
| Raspberry | — | — | 100% | — | 12.5% | | 12.5% | |
| Moss | — | — | — | 100% | 25% | | | 25% |
| ORAC Buffer | — | — | — | — | — | 37.5% | 37.5% | 25% |
| SUM | 100% | 100% | 100% | 100% | 100% | 100% | 100% | 100% |
| Experimental ORAC value (µM trolox) | 91 | 1648 | 3721 | 508 | 2898 | 198 | 2563 | 136 |

TABLE 9

Experiment no. 2

| | Experimental ORAC value (µM Trolox) | | Formulation 1 theoretical ORAC value (µM Trolox) by calculation |
|---|---|---|---|
| Dead Sea water I | 91 | 50% | 45.5 |
| Goji | 1648 | 12.5% | 206 |
| Raspberry | 3721 | 12.5% | 465 |
| Moss | 508 | 25% | 127 |
| SUM | | 100% | 843.7 |

The results of both studies are summarized in Table 10 below which provides a clear indication to the synergistic character of formulations of the invention. Specifically, the results indicate that a combination of the Dead Sea water with each of the Goji extract or the Moss extract was not beneficial. However, the combination of all three extracts with the Dead Sea water (Formulation 3) or the combination of the Raspberry extract alone with the Dead Sea water provided unique and unexpected combinations each demonstrating a synergistic effect.

TABLE 10

Synergism

| sample | ORAC Value (µM Trolox) | theoretical ORAC value (µM Trolox) by calculation | Proportion |
|---|---|---|---|
| Dead Sea water I | 91 | 45.5 | |
| Goji | 1648 | 206 | |
| Raspberry | 3721 | 465 | |
| Moss | 508 | 127 | |
| Formulation I | 2898 | 843.70 | 3.43 |
| Dead Sea water and Goji | 198 | 251.53 | 0.79 |

TABLE 10-continued

Synergism

| sample | ORAC Value (µM Trolox) | theoretical ORAC value (µM Trolox) by calculation | Proportion |
|---|---|---|---|
| Dead Sea water and Raspberry | 2563 | 510.69 | 5.02 |
| Dead Sea water and Moss | 136 | 172.59 | 0.79 |

It must be emphasized that while Table 10 also provides indication as to the activity of each of the components alone, the combination of the three plant extracts with the waters of the Dead Sea does not only provide antioxidant activity but also allows the use of much lower concentrations of each of the components, so as to avoid or minimize some of the toxicity associated with thereof. As such, the preparations of the invention are not only much more active as compared with the individual components but also are non-toxic and safe for human and animal use.

EXAMPLE 4

Human Skin Organ Culture Model for Biological Tests on Epidermis

Skin fragments were obtained with informed consent from 20-60 years old, healthy women, who underwent breast or abdomen reduction. Samples were cut into pieces of approximately 0.5×0.5 cm and placed, dermal side down and epidermal side up, in 35 mm diameter Petri dishes containing DMEM (Dulbecco's Modified Eagle's Medium) at 37° C., under 5% $CO_2$. A formulation of the invention and controls were applied on to the emerging epidermis, 24 hr before irradiation as described below. The samples were incubated for another 24 hr (epidermis viability, apoptosis level and inflammatory cytokine secretion), or 48 hr (epidermis viability). At the end of the post-irradiation period, epidermis was separated from dermis by 1-min heating in phosphate buffered saline (PBS) at 56° C. Remaining culture medium was collected.

A. Skin Exposure to UVB Irradiation

Before irradiation, all culture medium was discarded and the skin fragments were washed in PBS. Enough PBS was added to cover the dermis, and the sample was irradiated with a UVB source (VL-6.M lamp, peak emission 312 nm, filter size 145*48 mm, Vilber Lourmat, France) at 200 mJ/cm$^2$. Immediately after irradiation, PBS was replaced by DMEM growth medium, and skin was further incubated.

B. Apoptosis Determination by Caspase 3 Assay

Apoptosis was evaluated by caspase 3 assay. Epidermis samples were incubated in PBS containing 2.5 μM Ac-DEVD-AMC (fluorogenic caspase 3 substrate) with 0.02% triton x-100 and 10 mM DTT. The reaction was carried out at 37° C. in a 96-well plate. Fluorescence was measured using a Fluostar-BMG spectrofluorimeter at 390/435 nm. The activity slope was calculated over 30 min in linear range. Results were normalized with respect to MTT activity, measured after the caspase assay.

C. Viability Measurements by Mitochondrial Assay

Epidermis viability was estimated using a simple colorimetric assay of mitochondrial activity. Skin slices were heated in PBS at 56° C. for 1 min, and epidermis was separated as described above. Samples were transferred into wells containing 200 μl of 0.5 mg/ml (3-4,5-dimethylthiazol-2-yl)-2,5-diphenyl tetrazolium bromide ("MTT", Cat #475989, Calbiochem), and incubated 1 hr at 37° C. Resulting stain was extracted from formazan crystals in 0.5 ml of isopropanol, at room temperature for 30 min. 100 μl aliquotes were transferred into a 96 well plate, and optical density was measured separately for all four replicates at 570 nm.

D. Cytokine Secretion

Cytokines concentrations in culture media were measured by solid phase ELISA. Briefly, a polystyren microtiter plate was coated with a cytokine-specific monoclonal antibody. Standards and samples were then placed in the wells and incubated with the immobilized antibody. After immune binding of the antigen, unspecific compounds were washed away, and a second enzyme-linked, monoclonal or polyclonal antibody directed to the same antigen, was added. After completion of a "sandwich" binding, unspecific molecules were washed away, and a colorogenic substrate was added to reveal the enzyme-linked antibody. Cytokine concentrations were determined by comparison with the standards.

Results:

As FIG. 1 (Irradiation with UVB (280-320 nm) at 200 mJ/cm$^2$) demonstrates, the skin organ displayed a statistically significant increase of the caspase-3 activity (control) in response to UV irradiation compared with non-irradiated control. Topical application of a gel preparation (containing Formulation 1) comprising citric acid as the carrier showed a significant decrease in caspase-3 activity (known to be involved in the final stages of apoptotic processes) in response to UV irradiation as compared with irradiated skin with gel containing citric acid only (results not shown). This clearly demonstrates that the formulation of the invention protected the skin from UV-induced apoptosis.

Figure 2:
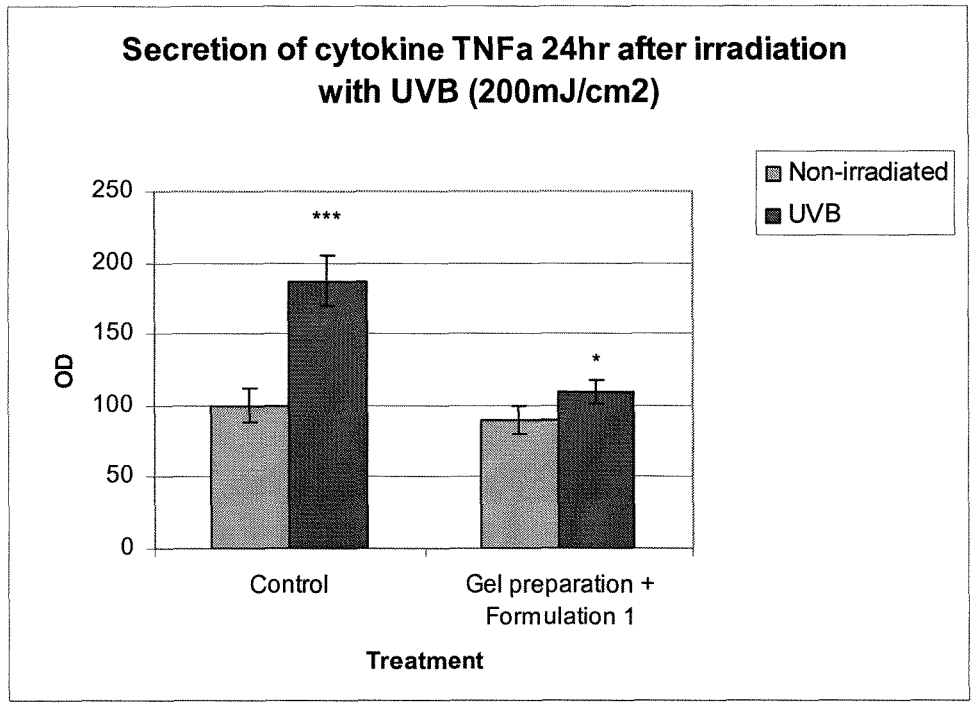
FIG. 2 demonstrates the secretion of cytokine TNF-α 24 hours after irradiation with UV-B.

As FIG. 2 shows, the skin organ displayed a statistically significant increase of TNF-α in response to UV irradiation as compared with non-irradiated skin (control). Topical application of gel containing citric acid only prior to irradiation showed no significantly difference to UVB-irradiated control, but topical application of gel containing citric acid with the Formulation 1, prior to irradiation, showed a significant decrease ($p<0.01$) in TNF-α secretion compared to UVB-irradiated control.

As TNF-α is a pro-inflammatory cytokine, its levels increase when inflammation occurs. The data demonstrates that the formulation of the invention protected the skin from UV-induced inflammation.

EXAMPLE 5

Toxicity

As the toxicity results indicate, the use of the individual extracts while being beneficial (see the above ORAC tests) may impose toxicity when used in high doses. When the extracts are combined according to the present invention, the quantity of each individual component in the composition may remain low, so as to avoid toxicity, while maintaining at least the same biological effect. As shown above, the compositions of the invention have also exhibited synergism.

TABLE 11

Toxicity of each of the components of compositions of the invention.

| Material tested | Proliferation | Toxicity | Comments |
| --- | --- | --- | --- |
| Deep Sea Water | Optimal concentration about 1.25% | LC50 > 5% | Toxicity determined according to MTT assay; Alamar Blue assay did not detect toxicity even for 5%-10%. |
| Himalayan Raspberry Root Extract | Optimal concentration about 0.1%-0.5% | LC50 = 2.5% | |
| Iceland Moss Extract | Optimal concentration about 1.25% | LC50 > 10% | |
| Goji Berries Extract | Not detected | LC50 > 10% | |
| Dead Sea water II | Optimal concentration about 0.25% | LC50 ≈ 2% | Toxic effect observed already at 1% concentration. No significant differences from Dead Sea I in terms of proliferation and cytotoxicity. |

The invention claimed is:

1. A composition, comprising:
   Dead Sea water;
   an extract of the Himalayan Raspberry (*Rubus ellipticus*);
   an extract of the Goji Berry (*Lycium Barbarum*); and
   an extract of the Iceland moss (*Cetraria islandica*), wherein a ratio of active components of the extract of Himalayan Raspberry to the extract of Goji Berry to the extract of Iceland moss in the composition is 0.05:1:2.

2. The composition according to claim 1, further comprising one or more natural materials, in the form of a single material or a mixture of natural materials, the one or more natural materials being obtained from waters of the Dead Sea, mud surrounding the Dead Sea, and/or soil bed of the Dead Sea.

3. The composition according to claim 1, wherein the Dead Sea water has a specific density of 1.25-1.35 g/ml, a pH of 4.6-5.6 (at 25° C.), and less than 100 cfu/g of non-pathogenic microbes.

4. The composition according to claim 3, wherein the Dead Sea water comprises $Ca^{+2}$, $Cl^-$, $Mg^{+2}$, $Na^+$, $K^+$ and $Br^-$.

5. The composition according to claim 1, wherein at least one extract selected from an extract of Himalayan Raspberry (*Rubus ellipticus*), an extract of Goji Berry (*Lycium Barbarum*), and an extract of Iceland moss (*Cetraria islandica*) is a pure (neat) botanical extract or an extract formulated with at least one additive.

6. The composition according to claim 1, wherein the composition is for topical application.

7. The composition according to claim 1, being in a form selected from the group consisting of a lotion, an ointment, a gel, a cream, a water in oil or oil in water emulsion, a shampoo, a moisturizer, a sunscreen, a cream, a stick, a spray, an aerosol, foam, a paste, a mousse, a solid, semi-solid, or a liquid make-up, a foundation, and an eye make-up.

8. The composition according to claim 1, further comprising at least one additive selected from the group consisting of a diluent, a preservative, an abrasive, an anticaking agent, an antistatic agent, a binder, a buffer, a dispersant, an emollient, an emulsifier, a co-emulsifiers, a fiberous material, a film forming agent, a fixative, a foaming agent, a foam stabilizer, a foam booster, a gellant, a lubricant, a moisture barrier agent, a plasticizer, a preservative, a propellant, a stabilizer, a surfactant, a suspending agent, a thickener, a wetting agent, and a liquefier.

9. The composition according to claim 1, further comprising at least one additive selected from the group consisting of an anti-acne agent, an anti-aging agent, an antibacterial agent, an anti-cellulites agent, an antidandruff agent, an antifungal agent, an anti-inflammatory agent, an anti-irritation agent, an antimicrobial agent, an antioxidant agent, an antiperspirant agent, an antiseptic agent, a cell stimulant, a cleansing agent, a conditioner, a deodorant, a depilatory, a detergent, an enzyme, an essential oil, an exfoliant, a fungicide, a glosser, hair conditioner, hair set resin, hair sheen agent, hair waving agent, a humectants, a moisturizer, an ointment base, a perfume, a protein, a skin calming agent, a skin cleanser, a skin conditioner, a skin healing agent, a skin lightening agent, a skin protectant, a skin smoothing agent, a skin softening agent, a skin soothing agent, a sunscreen agent, a tanning accelerator, vitamins, a colorant, and a flavoring agent.

10. The composition according to claim 1, further comprising deep seawater.

11. A method for protecting and/or improving the state of the skin of a subject and/or treating imperfections of the skin of a subject in need thereof, the method comprising:
    topically administering the composition according to claim 9 onto the skin of the subject.

12. The method according to claim 11, for treating rings under the eye, symptoms of aging, protecting the skin, increasing the detoxification of xenobiotics, intervening on pigmentation level, inhibiting melanogenesis, protecting the body against ionizing pollution, stimulating the detoxification systems, stimulating hair and body hair growth, modulating DHT levels, and/or promoting lipolysis.

13. The method according to claim 11, wherein the disease or disorder of the skin is related to sun exposure or is a secondary condition, being related to an existing condition or inflammation.

14. The method according to claim 11, wherein the disease or disorder of the skin is age-related.

15. The method according to claim 11, wherein the disease or disorder of the skin is selected from the group consisting of a wound, acne, psoriasis, atopic skin, diabetic skin, dermatitis, eczema, xerotic skin, dry skin, and chaffed skin.

16. A method for protecting the skin of a subject from UV-induced disease or disorder, the method comprising:
    applying to the skin of said subject the composition according to claim 1.

17. The method according to claim 16, wherein the UV-induced disease or disorder is apoptosis or inflammation.

18. A lotion, an ointment, a gel, a shampoo, a moisturizer, a sunscreen, a cream, a stick, a spray, an aerosol, foam, a paste, a mousse, a solid, semi-solid, or a liquid make-up, a foundation, or an eye make-up, comprising:
    the composition according to claim 1.

* * * * *